United States Patent [19]
Eaton et al.

[11] Patent Number: 5,066,272
[45] Date of Patent: Nov. 19, 1991

[54] MAGNETIC NERVE STIMULATOR

[75] Inventors: Harry A. C. Eaton, Columbia; Robert S. Fisher, Cockeysville, both of Md.

[73] Assignee: The Johns Hopkins University, Baltimore, Md.

[21] Appl. No.: 545,801

[22] Filed: Jun. 29, 1990

[51] Int. Cl.$^5$ ............................................... A61N 1/00
[52] U.S. Cl. ........................................ 600/9; 600/14; 128/421
[58] Field of Search ............... 600/9, 13, 14; 128/421, 128/422, 419 F

[56] References Cited

U.S. PATENT DOCUMENTS

| | | | |
|---|---|---|---|
| 3,698,398 | 10/1972 | Berkovits | 128/422 |
| 3,841,306 | 10/1974 | Hallgren | 600/13 |
| 4,121,594 | 10/1978 | Miller et al. | 128/422 |
| 4,672,951 | 6/1987 | Welch | 128/1.5 |
| 4,940,453 | 7/1990 | Cadwell | 600/13 |
| 4,974,114 | 11/1990 | Kammerer | 600/9 |

Primary Examiner—Francis Jaworski
Assistant Examiner—George Manuel
Attorney, Agent, or Firm—Robert E. Archibald; Francis A. Cooch

[57] ABSTRACT

A magnetic nerve stimulator comprises a capacitor which is charged to a high voltage, then discharged through a coil placed near the head. The magnetic field produced induces eddy currents in the brain that stimulate neurons. When the capacitor is fully discharged, the discharge path is broken by opening a switch. The inductive action of the coil forces a diode to turn on and the energy from the collapsing magnetic field around the coil charges a second capacitor. The charge on the second capacitor is augmented by a power source to make up for any losses, and the process is repeated. The stimulator of the invention can pulse rapidly, does not cause excessive heating of the coil, and uses comparatively little energy. As a result, high level cognitive functions in the brain can be disrupted for diagnostic purposes.

29 Claims, 1 Drawing Sheet

Inductor current

100 μs

Induced voltage

Inductor current 2,800 A

350 μs

Induced voltage

MAGNETIC NERVE STIMULATOR

BACKGROUND OF THE INVENTION

The invention relates to magnetic nerve stimulators and, more specifically, to a stimulator capable of producing a rapid train of large amplitude, short duration magnetic pulses.

Nerve stimulation and stimulators are important diagnostic tools in medicine today. Both electrical and magnetic means are employed to stimulate brain tissue and peripheral nerves. Existing stimulators are useful for exploring cognitive phenomenon, measuring central nerve conduction velocity, and intraoperative monitoring of spinal cord trauma during surgery. However, existing stimulators are inadequate for use in detailed mapping of the brain's functional (e.g., speech, vision, etc.) areas, peripheral nerve stimulation in situations requiring comfort and relaxation, and intraoperative monitoring of the front of the spinal cord.

Patients with seizures or brain tumors may require that a portion of their brain be removed. For example, if medical treatment of epilepsy patients is ineffective, an alternative is to remove that portion of the brain containing the epilepsy seizure focus. However, the seizure focus may be located next to a functionally important area of the brain.

To tailor the operation for removal of the seizure focus only, the brain is mapped in specialized epilepsy units using electrical stimulation. Generally, two mappings of the brain are made, one to locate the seizure focus, the second to locate nearby functional areas. For example, to locate the brain's functional area responsible for speech, two techniques are currently used prior to seizure surgery. The first consists of removing portions of the scalp and skull to permit placement of electrodes in a grid pattern directly on the brain. Electrical stimulation is then used to generate a mapping. The second technique consists of putting one half of the brain to sleep with an injection in order to determine which half controls speech. While both techniques are useful, they are not always successful and, most importantly and obviously, they are very invasive.

Certain patients with brain tumors also require brain mapping to preserve functional areas from being damaged during surgery to remove the tumor. While magnetic resonance imaging can locate the tumor, it is an anatomical test and does not provide information on the function of areas of the brain located close to the tumor.

Peripheral nerve stimulation is used to define nerve injuries and/or malfunction resulting from trauma, back injury, diabetes, peripheral neuropathies, etc. This is currently done by electrical devices which by giving repetitive shocks to nerve can be used to measure velocity and amplitude of signals carried by the nerve. For example, if a patient's hand is numb due to nerve damage from an industrial accident, an electrical stimulator can be used to determine nerve function near the elbow and, hence, the extent and location of the injury to the nerves.

A problem with using electrical stimulation in testing peripheral nerves is that the electrical shocks while tolerable are uncomfortable. Also, a pulse rate which is tolerable is insufficient to obtain good results for a subset of tests that are used in peripheral nerve stimulation.

Nerve stimulation is used in intraoperative monitoring to warn a surgeon if he or she is adversely affecting the spinal cord or brainstem. An electrical stimulator is used to obtain the somatosensory evoked potential by stimulating the peripheral nervous system. Stimuli to skin or nerve will evoke nerve signals that travel to the cortex region of the brain and the response to the stimulus is recorded, in either a continuous or intermittent fashion, during this process. If the surgeon compresses the spinal cord too much, e.g., during decompression of a disk, the response signals will disappear giving the surgeon an opportunity to readjust. The problem with somatosensory evoked potentials, however, is that they only test the back part of the spinal cord and it is the front part that is most likely to be damaged during many types of surgery.

A method for testing the front part of the spinal cord is to use a magnetic stimulator near the motor control region of the brain. This will obtain a motor evoked potential (MEP) which is the reverse of an evoked potential in that an MEP signal travels from the brain to the periphery rather than from the periphery to the brain. Most importantly, the MEP signal travels from the brain down the front of the spinal cord. Unfortunately, existing magnetic stimulators pulse at most once per second which is too slow to obtain sufficient numbers of MEPs to provide immediate feedback to the surgeon.

Current magnetic nerve stimulators (FIG. 1) operate by discharging a large electric charge stored in a capacitor through a coil placed near the head or nerves of a human or animal. They are an improvement over electrical stimulators because they can be used in brain mapping without opening the skull, i.e., noninvasively; they are significantly less painful; and, as noted above, they can be used to generate motor evoked potentials to test the front part of the spinal cord as part of intraoperative monitoring.

However, shortcomings remain. As noted with intraoperative monitoring, the pulse repetition rate is extremely low. This results from the need to recharge the energy storing capacitor. Recharging is usually done through a high voltage DC power supply with a resistor or resistor-inductor circuit to limit the peak current demand from the power supply.

Slow pulse repetition rate precludes the possibility of disruption of high level cognitive function required for proper brain mapping. Present stimulators are only useful for producing motor twitching, motor evoked potentials, or brief visual stimulation. High order functions such as speech, memory, or behavior cannot be disrupted by slow pulse rates. This makes it impossible to perform cognitive functional mapping such as language mapping with these devices. The slow pulse repetition rate also results in very long times being needed to perform the signal averaging necessary to measure nerve potentials.

A final problem with present magnetic stimulators arises from the large amounts of heat which are dissipated in the stimulating coil which is placed near the body. Nearly all of the energy of each pulse is converted to heat in the coil during the stimulation pulse. Coil heating limits the time of operation as well as the pulse repetition rate in order to avoid burning the subject or damaging the apparatus.

In sum then, what is needed is a magnetic stimulator that can be used to map functional areas of the brain effectively and noninvasively; that can stimulate peripheral nerves less painfully and more rapidly; and that can pulse rapidly enough to obtain sufficient motor evoked potentials to be an effective intraoperative monitor.

SUMMARY OF THE INVENTION

The magnetic nerve stimulator of the invention solves the above problems by recapturing the energy stored in the magnetic field which is automatically expelled from the field surrounding the coil. A first capacitor is fully charged to store the energy for a pulse, then discharged through the stimulating coil upon closure of a first switch. When all of the capacitor energy is transferred to the coil, the first switch opens and the energy from the collapsing magnetic field is used to charge a second capacitor. A second switch closes and discharges this capacitor through the coil producing the next stimulation pulse. The second switch then opens and the collapsing magnetic field energy recharges the first capacitor. The cycle is then repeated as often as is required for a particular patient.

It is therefore an object of the present invention to provide a magnetic nerve stimulator which can pulse rapidly because the capacitors are nearly fully recharged by the energy recovery process; therefore, less time is needed to "top off" the charge to make up for small energy losses in the system to get ready for the next pulse.

A second object of the invention is to provide for less heat dissipation in the stimulation coil. Since the energy is reclaimed into a capacitor, much less is converted to heat in the coil.

A third object of the invention is to consume less power from the power supply because the magnetic field energy generated in the magnetic nerve stimulator is recaptured.

A fourth object of the invention is to allow polarized capacitors to be used for energy storage. The voltage across each capacitor will always have the same polarity with the circuit of the invention.

For a more complete appreciation of the present invention, including other objects, purposes and characteristic features, attention is invited to the following detailed description of a preferred embodiment taken with the figures of the drawings. The scope of the invention, however, is limited only through the claims appended hereto.

DETAILED DESCRIPTION OF THE PREFERRED EMBODIMENT

Figure 2A:
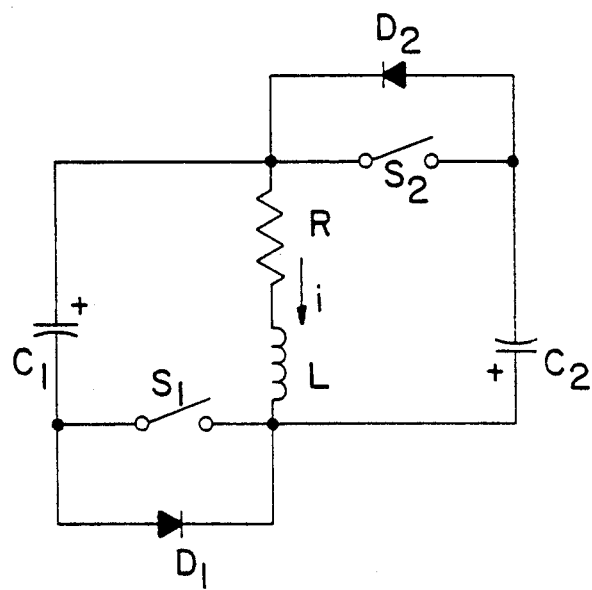
FIG. 2, consisting of FIGS. 2a and 2b, shows a circuit diagram embodying the principles of the magnetic nerve stimulator of the present invention, along with the waveforms of the coil current and induced voltage in the tissue.

The magnetic nerve stimulator circuit shown in FIG. 2a implements the energy recapturing scheme of the present invention. A first capacitor $C_1$ initially charged by a power supply (not shown), e.g., of the switch mode type, then first switch $S_1$ is closed. As in conventional stimulators this discharges first capacitor $C_1$ through the coil L, inducing a stimulation pulse.

Figure 1A:
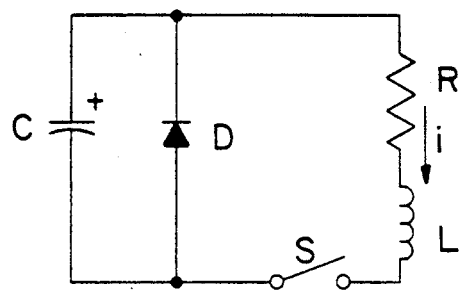
FIG. 1, consisting of FIGS. 1a and 1b, shows the circuit diagram of a typical magnetic nerve stimulator presently used, along with the waveforms of the coil current and induced voltage in the tissue.
Figure 1B:
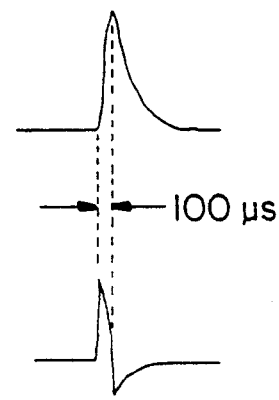

When the current in the coil L has reached its peak value, i.e., the voltage across first capacitor $C_1$ equals zero, first switch $S_1$ is opened. Inductive action from the coil L will turn on second diode $D_2$ and force current to flow into second capacitor $C_2$. The majority of the energy resulting from the discharge of first capacitor $C_1$ through the coil L and the subsequent collapsing magnetic field around the coil L will flow as current to and be saved in second capacitor $C_2$. As a result, coil L heating will be much less than in the conventional stimulator circuit (FIG. 1), because only the energy lost during the stimulation pulse will convert to heat. Then, the electric charge in second capacitor $C_2$ will be supplemented from a switch mode power supply (not shown), in order to replace energy lost during the first stimulation pulse.

Second switch $S_2$ is used to discharge second capacitor $C_2$ through the coil L to produce the next stimulus pulse. When the voltage across second capacitor $C_2$ reaches zero, i.e., inductor current reaches a maximum, second switch $S_2$ opens. This action recharges first capacitor $C_1$ via first diode $D_1$. After supplementing the charge of first capacitor $C_1$ by the power supply, the system is ready to repeat the cycle.

An alternative to the above embodiment is to eliminate the diodes $D_1$ and $D_2$. Then when each switch ($S_1$ or $S_2$) opens after discharging its respective capacitor, the other switch would close simultaneously to permit charging of its capacitor. The switch would then open to avoid causing its capacitor to discharge before it is "topped off" by the power supply. Finally, the switch is closed again to discharge the capacitor once it is fully charged.

The resistor, R, shown in FIG. 2a represents the sum of resistance in the coil L, cables, capacitors and switches. This resistance is minimized in order to produce the largest possible stimulation, and to maximize recapture of useful energy for the next pulse.

The direction of the induced electric field will reverse from pulse to pulse with this method. A relay, or solid state switches, can be used to reverse the coil L connections between pulses so that the electric field does not reverse from pulse to pulse. This relay would only be required to switch states while conducting zero current.

Figure 2B:
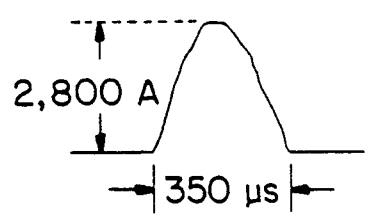
Figure 2B:

FIG. 2b shows the waveform of the current through the coil L, and induced voltage in an adjacent conducting medium for this device. The induced voltage comprises a positive pulse, followed immediately by a negative pulse of nearly equal amplitude.

As noted above, a switch mode power supply can be used for initial charging, and subsequent "topping off" of the capacitor charge. This is more efficient, consumes less power, and can charge faster than charging from a DC power supply.

The magnetic nerve stimulator circuit of the present invention as described above requires switches capable of interrupting very large currents. Any switching technology capable of switching very large currents in short time intervals could be used, e.g., solid state "gate turn-off thyristors" able to switch off currents of up to 1,400 Amperes. Parallel connection of such switches could provide larger current switching ability. The switching action of first and second switches $S_1$ and $S_2$ could be delayed until the diode has turned on, resulting in a division of the inductor current prior to the switching action. This will lower the current that must be turned off by the switch, but will result in slight negative charging of the capacitor. Conventional brain stimulators use peak currents of up to 5,000 Amperes. Equivalent stimulation at lower switched current may be achieved by using a coil with more windings, but lower peak current, or through the use of transformer coupling to the stimulus coil L.

Thus, the present invention provides a magnetic nerve stimulator circuit and stimulation method for producing a rapid train of large amplitude, short duration pulsed magnetic fields for non-invasive stimulation of animal or human brain tissue. The pulses are capable of inducing eddy currents in nearby brain tissue of sufficient strength and duration to cause tissue stimulation, and disruption of high level cognitive function and, therefore, will be useful in performing functional mapping of the brain. The invention can also stimulate peripheral nerves and provide measurements of nerve conduction velocity for disease diagnosis, or motor evoked potentials for surgical monitoring.

The invention pulses rapidly, does not cause excessive heating of the coil, and uses comparatively little energy. Finally, the capacitor voltages will always have the same polarity resulting in lower dielectric absorption losses and increased capacitor life.

We claim:

1. A magnetic nerve stimulator comprising:
   power supplying means for supplying electric charge;
   at least two capacitor means connected to said power supplying means for accumulation said electric charge from said power supplying means;
   a coil connected to said capacitor means, said coil producing a magnetic pulse when one of said capacitor means discharges said electric charge through said coil and said coil forcing an electric current induced by the magnetic field energy from said coil to charge another of said capacitor means; and
   at least two switching means for connecting and disconnecting said capacitor means to said coil to permit the charging and discharging of each of said capacitor means by turns.

2. The stimulator as recited in claim 1, further comprising at least two diode means connected between said coil and said capacitor means, said diode means being turned on by an inductive action from said coil forcing an electric current induced by the magnetic field energy from said coil to charge said capacitor means.

3. The stimulator as recited in claim 1, wherein said stimulator produces a rapid train of large amplitude, short duration magnetic pulses, said train of pulses being sufficient to cause disruption of high level cognitive function in a human brain.

4. The stimulator as recited in claims 1, 2 or 3, wherein said power supplying means comprises a switch mode power supply.

5. The stimulator as recited in claims 1, 2 or 3, further comprising a relay means connected to said coil to reverse said coil's connections between said magnetic pulses to prevent the direction of said magnetic field energy from reversing with each of said pulses.

6. The stimulator as recited in claim 5, wherein said relay means comprises a solid state switch.

7. The stimulator as recited in claims 1, 2 or 3, wherein said switching means comprise solid state gate turn-off thyristors.

8. The stimulator as recited in claim 7, wherein said thyristors are connected in parallel.

9. The stimulator as recited in claim 1, 2 or 3, wherein a sum of resistance in said coil, said capacitor means, said switching means, and a cable connecting said coil, said capacitor means, and said switching means is minimized.

10. A magnetic nerve stimulator comprising:
    power supplying means for supplying electric charge;
    at least two capacitor means connected to sad power supplying means for accumulating said electric charge from said power supplying means;
    a coil connected to said capacitor means, said coil producing a magnetic pulse when one of said capacitor means discharges said electric charge through said coil;
    at least two switching means for alternately connecting and disconnecting said capacitor means to said coil;
    at least two diode means connected between said coil and said capacitor means, said diode means being turned on by an inductive action from said coil forcing an electric current induced by the magnetic field energy from said coil to charge said capacitor means; and
    a relay means connected to said coil to reverse said coil's connections between said magnetic pulses to prevent the direction of said magnetic field energy from reversing with each of said pulses;
    wherein a sum of resistance in said coil, said capacitor means, said switching means, and a cable connecting said coil, said capacitor means, and said switching means is minimized.

11. The stimulator ar recited in claim 10, wherein said stimulator produces a rapid train of large amplitude, short duration magnetic pulses, said train of pulses being sufficient to cause disruption of high level cognitive function in a human brain.

12. A circuit for producing a rapid train of large amplitude, short duration magnetic pulses comprising:
    power supplying means for supplying electric charge;
    at least two capacitor mans connected to said power supplying means for accumulating said electric charge from said power supplying means;
    a coil connected to said capacitor means, said coil producing a magnetic pulse when one of said capacitor means discharges said electric charge through said coil and said coil forcing an electric current induced by the magnetic field energy from said coil to charge another of said capacitor means; and
    at least two switching means for connecting and disconnecting said capacitor means to said coil to permit the charging and discharging of each of said capacitor means by turns.

13. The circuit as recited in claim 12, further comprising at least two diode means connected between said coil and said capacitor means, said diode means being turned on by an inductive action from said coil forcing an electric current induced by the magnetic field energy from said coil to charge said capacitor means.

14. A method for magnetically stimulating nerves comprising the steps of:
    initially charging a first capacitor means with an electric charge;
    discharging said first capacitor means through a coil by closing a first switching means thereby inducing a magnetic pulse;
    disconnecting said first capacitor means from said coil by opening said first switching means;
    charging a second capacitor means using said coil's magnetic field energy;

discharging said second capacitor means through said coil by closing a second switching means;

disconnecting said second capacitor means from said coil by opening said second switching means;

charging said first capacitor means using said coil's magnetic field energy; and repeating said discharging, disconnecting, and charging steps alternating between said first and said second capacitor means.

15. The method as recited in claim 14, further comprising the step of producing a rapid train of large amplitude, short duration magnetic pulses, said train of pulses being sufficient to cause disruption of high level cognitive function in a human brain.

16. The method as recited in claims 14 or 15, further comprising the step of supplying additional electric charge form a power supplying means to each of said first and said second capacitor means after each of said charging steps to fully charge each of said first and second capacitor means.

17. The method as recited in claim 16, wherein said power supplying means comprises a switch mode power supply.

18. The method as recited in claim 16, further comprising the step of minimizing a sum of resistance in said coil, said capacitor means, said switching means, and a cable connecting said coil, said capacitor means, and said switching means to maximize recapture of said coil's magnetic field energy.

19. The method as recited in claim 18, further comprising the step of reversing said coil's connections between said magnetic pulses to prevent the direction of said magnetic field energy from reversing with each of said pulses.

20. The method as recited in claim 19, wherein said first and said second switching means comprise solid state gate turnoff thyristors.

21. The method ass recited in claim 20, wherein said thyristors are connected in parallel.

22. The method as recited in claims 14 or 15, wherein said charging steps each comprises the step of turning on a first or second diode means using an inductive action from said coil to force an electric current to flow into said first or said second capacitor means, respectively.

23. The method as recited in claim 22, further comprising the step of delaying each of said disconnecting steps until said first or said second diode means has turned on to lower said electric current that must be turned off by said first or said second switching means.

24. The method as recited in claims 14 or 15, wherein said step of charging a second capacitor means comprises the steps of:

closing said second switching means simultaneously with the opening of said first switching means to permit an electric current induced by the magnetic field energy from said coil to charge said second capacitor means; and opening said second switching means before said second capacitor means discharges.

25. The method as recited in claim 24, wherein said step of charging said first capacitor means comprises the step of:

closing said first switching means simultaneously with the opening of said second switching means to permit an electric current induced by the magnetic field energy from said coil to charge said first capacitor means; and opening said first switching means before said first capacitor means discharges.

26. A method for magnetically stimulating nerves comprising the steps of:

initially charging a first capacitor means with an electric charge;

discharging said first capacitor means through a coil by closing a first switching means thereby inducing a magnetic pulse;

disconnecting said first capacitor means form coil by opening said first switching means;

turning on a second diode means using an inductive action from said coil to force an electric current to flow into a second capacitor means to charge said second capacitor means;

supplying additional electric charge from a power supplying means to said second capacitor means to fully charge said second capacitor means;

revering said coil's connections;

discharging said second capacitor means through said coil by closing a second switching means;

disconnecting said second capacitor means from said coil by opening said second switching means;

turning on a first diode means using an inductive action from said coil to force an electric current to flow into said first capacitor means to charge said first capacitor means;

supplying additional electric charge from said power supplying means to said first capacitor means to fully charge said first capacitor means;

reversing said coil's connections;

repeating said discharging, disconnecting, turning on, supplying, and reversing steps alternating between said first and said second capacitor means; and producing a rapid train of large amplitude, short duration magnetic pulses, said train of pulses being sufficient to cause disruption of high level cognitive function in a human brain;

wherein a sum of resistance in said coil, said capacitor means, said switching means, and a cable connecting said coil, said capacitor means, and said switching means is minimized to maximize recapture of said coil's magnetic field energy.

27. A method for producing a rapid train of large amplitude, short duration magnetic pulses comprising the steps of:

initially charging a first capacitor means with an electric charge;

discharging said first capacitor means through a coil by closing a first switching means thereby inducing a magnetic pulse;

disconnecting said first capacitor means from said coil by opening said first switching means;

charging a second capacitor means using said coil's magnetic field energy;

discharging said second capacitor means through said coil by closing a second switching means;

disconnecting said second capacitor means from said coil by opening said second switching means;

charging said first capacitor means using said coil's magnetic field energy; and repeating said discharging, disconnecting, and charging steps alternating between said first and said second capacitor means.

28. The method as recited in claim 27, further comprising the step of supplying additional electric charge from a power supplying means to each of said first and said second capacitor means after each of said charging steps to fully charge each of said first and said second capacitor means.

29. A method for producing a rapid train of large amplitude, short duration magnetic pulses comprising the steps of:
    initially charging a first capacitor means with an electric charge;
    discharging said first capacitor means through a coil by closing a first switching means thereby inducing a magnetic pulse;
    disconnecting said first capacitor means from said coil by opening said first switching means;
    turning on a second diode means using an inductive action from said coil to force an electric current to flow into a second capacitor means to charge said second capacitor means;
    supplying additional electric charge from a power supplying means to sad second capacitor means to fully charge said second capacitor means;
    reversing said coil's connections;
    discharging said second capacitor means through said coil by closing a second switching means;
    disconnecting said second capacitor means from said coil by opening said second switching means;
    turning on a first diode means using an inductive action from said coil to force an electric current to flow into said first capacitor means to charge said first capacitor means;
    supplying additional electric charge from said power supplying means to said first capacitor means to fully charge said first capacitor means;
    reversing said coil's connections, and
    repeating said discharging, disconnecting, turning on, supplying, and reversing steps alternating between said first and said second capacitor means;
    wherein a sum of resistance in said coil, said capacitor means, said switching means, and a cable connecting said coil, said capacitor means, and said switching means is minimized to maximize recapture of said coil's magnetic field energy.

* * * * *